United States Patent [19]
Hashimoto et al.

[11] Patent Number: 5,719,050
[45] Date of Patent: Feb. 17, 1998

[54] ANIMAL CELL CULTURING MEDIA CONTAINING N-ACETYL-L-GLUTAMIC ACID

[75] Inventors: Makoto Hashimoto; Tsutomu Naito, both of Otawara, Japan

[73] Assignee: Eiken Chemical Co., Ltd., Tokyo, Japan

[21] Appl. No.: 357,379

[22] Filed: Dec. 16, 1994

[30] Foreign Application Priority Data

Dec. 24, 1993 [JP] Japan .................................. 5-347732
Jul. 1, 1994 [JP] Japan .................................. 6-173766

[51] Int. Cl.$^6$ .............................. C12N 5/02; C12N 5/06; C12N 5/08; C12N 5/12
[52] U.S. Cl. .................. 435/240.31; 435/41; 435/240.2; 435/240.3; 435/172.2; 530/808; 530/809
[58] Field of Search ........................... 435/240.31, 240.2, 435/240.3, 41, 172.2, 530

[56] References Cited

U.S. PATENT DOCUMENTS 4,927,762  5/1990  Darfler .................................. 435/325

FOREIGN PATENT DOCUMENTS

WO 00335  1/1986  WIPO .

OTHER PUBLICATIONS

The Biochemical Journal, vol. 221, No. 1 (Jul. 1984) 255–60.
The Journal of Clinical Investigation, vol. 90, No. 4 (Oct. 1992) 1386–95.
Chemical Abstracts, vol. 90, No. 17 (1979) 133118z.
Journal of Cell Science, vol. 68 (1984) 285–303.
Federation Proceedings, vol. 43, No. 1 (Jan. 1984) 121–25.
Biotechnology & Bioengineering, vol. 32, No. 8 (Oct. 1988) 1015–1028.
Biotechnology Letters, vol. 9, No. 4 (1987) 259–64.

*Primary Examiner*—Blaine Lankford
*Attorney, Agent, or Firm*—Fitzpatrick, Cella, Harper & Scinto

[57] ABSTRACT

The present invention relates to a medium composition for culturing animal cells which is obtained by combining at least one component selected from the group of substances mentioned below with a medium composition comprising inorganic salts, saccharides, vitamins and amino acids; a method for culturing animal cells comprising adding to a medium for the cells as a cell growth promoting substance at least one component selected from the group mentioned below; a method for enhancing the antibody production of antibody-producing cells comprising adding to a medium for the cells at least one component selected from the group mentioned below; a composition for enhancing the antibody production of antibody-producing cells which is obtained by combining at least one antibody production enhancing agent selected from the group mentioned below with a composition comprising inorganic salts, saccharides, vitamins and amino acids; and a method for producing a physiologically active substance comprising culturing animal cells on a medium containing at least one cell growth promoting substance selected from the group mentioned below, and then harvesting the cells grown or the substances produced by the cells.

D-penicillamine or salts thereof
Acetoacetic acid or salts thereof
Biguanides
Vitamin $K_5$ or salts thereof
N-acetyl-L-glutamic acid or salts thereof.

24 Claims, 12 Drawing Sheets

ANIMAL CELL CULTURING MEDIA CONTAINING N-ACETYL-L-GLUTAMIC ACID

BACKGROUND OF THE INVENTION

1. Field of the Invention

The present invention relates to a medium for culturing animal cells. More particularly, the present invention is concerned with a serum-free medium containing no serum as a medium component, a low protein medium which is serum free and yet whose protein content has been reduced as much as possible, and a protein-free medium containing no protein.

2. Description of the Prior Art

As life science has developed, there has increased a need to culture animal cells in vitro. Cells of a number of animal species produce useful substances which cannot be obtained from other materials, and it is significant to culture these cells in vitro. Furthermore, animal cells are important as host cells in transforming target cells with a vector wherein a gene coding for a useful protein has been inserted. Although cells of microorganisms, such as bacteria and yeast, are also used as a host cell, some proteins require the use of animal cells in many cases due to limitations with respect to the addition of sugar chains or expression-regulatory regions such as a promoter.

For example, in order to express the immunoglobulin gene which has been inserted in a vector, myeloma cells are often used as a host cell. Furthermore, fusion cells which will be the sources of supply of monoclonal antibodies, various lymphokines and the like are derived from animal cells.

In the culturing of animal cells, a synthetic medium is used which contains nutrients, such as carbohydrates, lipids, amino acids, vitamins, peptides, proteins and inorganic ions, as well as growth promoting factors, such as hormones and nucleosides. Known synthetic media include MEM (Science, 130, 432; 1959) used for culturing animal cells in general and RPMI1640 medium (J.A.M.A., 199, 519; 1967) used for culturing lymphocytes. Usually, these synthetic media alone are not sufficient to maintain the growth of cells, and appropriate growth factors are added thereto according to the properties of the cells to be cultivated.

Generally, biological materials, such as various serums, yeast extract and the hydrolysate of lactoalbumin, are added to a synthetic medium. Among all, serums are extremely important additives, exhibiting growth support activity on a wide range of animal cells. They are added to the medium regardless of the kind of cells to be cultured. At present, animal serums derived from different animals including human, equine, bovine, simian and avian are utilized in cell cultivation. Furthermore, with respect to the serum derived from bovine, for example, it is known that the cell growth promoting effect decreases in the following order: fetal calf serum (hereinafter referred to as "FCS")>new born calf serum (within 1 week from birth)>calf serum (within 6 months from birth)>bovine serum.

However, there are several problems in the additon of an animal serum to a medium. The first problem is that, since animal serums are biological materials, it is difficult to maintain their quality constant. As seen from the difference by age mentioned in the preceding paragraph, there is a great deviation in the quality of animal serums. In addition, even in the same bovine serum, its culture support ability varies depending on the production lot. Thus, such difference in effect makes it difficult to maintain constant culture conditions. For this reason, sometimes it is necessary to assay newly purchased animal serums for their culture support ability prior to their use. In particular, in a bioassay where analysis is conducted making the growth of animal cells as an indicator, the uniformity of culture conditions is the minimum requisite. However, as far as an animal serum is added, the uniformity of culture conditions is difficult to achieve. In addition, the use of a component with a great deviation in quality (animal serum) will disturb the stable supply of a medium.

The second problem is that the purification of a useful substance produced by animal cells may be interfered by a number of proteins contained in the animal serum added to the medium. An animal serum is a complex of a multiplicity of components. Furthermore, a culture supernatant contains not only the substances derived from the animal serum added to the medium but also the metabolites from the animal cells. As a result, the culture has an extremely complicated composition. The isolation of the useful substance therefrom is a heavy burden, and it is difficult to expect a high yield.

In particular, when producing such a substance like immunoglobulin that is also abundantly present in a normal serum by culturing animal cells, the presence of an animal serum added to the medium is very likely to become a great problem, because highly advanced purification techniques are required for the separation of human immunoglobulin from bovine immunoglobulin. For easy purification of a useful substance produced by cells, it would be advantageous if the medium could be serum free, and, if possible, at the same time protein free. However, it is extremely difficult to culture cells on a protein-free medium wherein even the addition of a growth promoting component such as insulin is not allowed. Therefore, currently various protein components are added unavoidably.

The third problem is that there cannot be denied a possibility of the infection of cultured cells through an animal serum. Since it is impossible to sterilize an animal serum with heat, its sterilizing operation is limited. Thus, a possibility of the contamination of cultured cells with an unknown virus or the like cannot be denied. At present, before the addition of an animal serum to a medium, the serum is checked for its infectivity and is treated with a membrane filter for sterilization in order to avoid the danger of contamination, but such procedures are not complete and make the culturing operation complicated.

The fourth problem is the cost of an animal serum. When an animal serum is added to a medium, the serum cost amounts to about 90% of the medium cost. Since the quality of a serum has a great deviation, it is neccesary to strictly select a serum with satisfactory quality in order to maintain the quality of the medium. The cost of a serum further increases when a strict quality control is demanded.

The fifth problem is the presence of cell growth inhibitory substances in an animal serum. As mentioned above, an animal serum is a collection of a multiplicity of components, wherein the presence of cell growth promoting components as well as cell growth inhibitory substances is known. Some kinds of cells are known to survive only for a short period on a serum-added medium, and their long-term culture is possible only on a serum-free medium. Furthermore, the antibodies and complements contained in an animal serum may have a toxic effect on cells.

Toward the solution of the above-mentioned problems peculiar to animal serums, there have been made various attempts to search for a substitute for an animal serum to thereby reduce the amount of an animal serum added to a medium (low serum medium), as well as investigations into a medium containing no serum (serum-free medium). Concretely, it has been confirmed that some decrease in the amount of use of an animal serum or, depending on the kind of cells, serum-free culture is possible by using the following substances or means:

insulin transferrin epidermal cell growth factor progesterone testosterone adjustment of amino acids vitamins mercaptoethanol fatty acids albumin lipoproteins bovine pituitary extract.

However, the effect of many growth promoting substances so far reported is not necessarily sufficient, and there is a strong tendency that the effect depends on the kind of cells. Therefore, animal serums are still used broadly. It might be a possible solution to prepare a chemically synthesized pseudo-serum which resembles the composition of an animal serum, but actually it is not realistic to chemically imitate an animal serum which has a multiplicity of components.

In addition, even if some decrease has been achieved in the amount of an animal serum to be added, the problem at the time of purification is still left if protein components are used in large quantities as substitutes for the serum. Considering the influence of proteins upon purification operation, a serum-free but protein-rich medium is not sufficient. Efforts are required to reduce the amounts of those protein components other than the serums as much as possible.

It is not known whether the above-mentioned growth promoting substances exhibit growth support ability to all kinds of the animal cells equally in a similar manner. Although a suitable medium composition is known for each of the established cell lines which are frequently used in various experiments, it cannot be expected that a specific medium composition suitable for one cell line exhibits a similar culture ability on another cell line of a different origin. In many cases, it is necessary to establish a suitable medium composition for each kind of cells through experience. Therefore, it is preferable to have a greater number of growth promoting substances which can be added to a medium, since they provide a wider range of choice according to the use of the medium.

On the other hand, in the cultivation of animal cells for the purpose of obtaining a useful substance, such as antibodies, the most important point for a growth promoting substance is to support the production of the target useful substance, needless to say its ability to culture the cells themselves. Not only growing the cells but also inducing the target substance as much as possible and easily recovering it are important. From such a viewpoint, there have been reports on cycloheximide, actinomycin D and the like which induce the production of interferon by, for example, human fibroblasts, but sufficient information has not yet been obtained on the production of antibodies. In addition, although substances such as cycloheximide, actinomycin D, sodium butyrate and vitamin A acid, have an action of inducing the production of a specific substance, they have cytotoxicity and thus are not desirable components for a medium. As so far mentioned, there have been a relatively small number of reports on those substances which are effective in enhancing substance production, and no substance has been known yet which exhibits an action of enhancing antibody production in a protein free medium which is advantageous with respect to purification.

OBJECTS AND SUMMARY OF THE INVENTION

It is an object of the present invention to search for novel cell growth promoting substances and to provide a serum-free medium. Further, it is another object of the present invention to provide techniques which can realize a low protein medium which is not only serum free but contains proteins only in traces or even a protein-free medium containing no protein.

It is still another object of the present invention to provide a serum-free medium which is suitable for the culture of antibody-producing cells, in particular those host cells which are transformed with a vector wherein the immunoglobulin gene has been inserted, as well as techniques for producing immunoglobulin using this medium. In addition, the present invention provides techniques for producing not only antibodies but also various physiologically active substances which can be obtained by culturing animal cells.

According to the present invention, the above-mentioned assignments are solved with a medium composition for culturing animal cells which is obtained by combining at least one component selected from the group of substances listed below with a medium composition comprising inorganic salts, saccharides, vitamins and amino acids. Furthermore, the present invention provides a method for culturing animal cells comprising adding to a medium for the cells as a cell growth promoting substance at least one component selected from the group mentioned below; a method for enhancing the antibody production of antibody-producing cells comprising adding to a medium for the cells at least one component selected from the group mentioned below; a composition for enhancing the antibody production of antibody-producing cells which is obtained by combining at least one antibody production enhancing agent selected from the group mentioned below with a composition comprising inorganic salts, saccharides, vitamins and amino acids; and a method for producing a physiologically active substance comprising culturing animal cells on a medium containing at least one cell growth promoting substance selected from the group mentioned below, and then harvesting the cells grown or the substances produced by the cells.

D-penicillamine or salts thereof

Acetoacetic acid or salts thereof

Biguanides

Vitamin $K_3$ or salts thereof

N-acetyl-L-glutamic acid or salts thereof

In the specification, each concentration of substances to be added expresses the final concentration in the cultivation of cells.

D-penicillamine to be used in the present invention is obtained as a decomposition product of penicillin. D-penicillamine is used as a therapeutic agent for rheumatism, Wilson's disease and the like, and is available in the market. However, there has been no reported use of D-penicillamine for culturing animal cells. D-penicillamine may be used in a salt form, such as a hydrochloride.

D-penicillamine is added to various synthetic basal media aseptically. The amount to be added is about 0.5–5000 mg per liter of the medium, preferably about 5–500 mg per liter. The more the amount falls away from the above range, the less the effect becomes, though still better results can be obtained compared to the case of no D-penicillamine added.

Acetoacetic acid to be used in the present invention is available in the market, but there has been no reported use of this substance for culturing animal cells. Acetoacetic acid is aseptically added to a synthetic basal medium in a salt form, such as a lithium salt. In addition to a lithium salt, a sodium salt or potassium salt may be used, but a lithium salt is most effective in cell growth. The amount to be added is about 0.005–50 mg per liter of the medium in the form of lithium acetoacetate, preferably about 0.01–10 mg per liter. The addition of an extremely small amount of acetoacetic acid or salts thereof produces an extremely great cell growth promoting effect or antibody production enhancing effect. However, an increase of the amount of addition does not remarkably improve the cell growth promoting effect or antibody production enhancing effect, and is likely to results in a decrease in such effect, though only a little.

Biguanides to be used in the present invention have an action of promoting the use of glucose by cells. Biguanides is a collective name of those drugs sold in the market as hypoglycemic agents which utilize the above-mentioned action. At presents, buformin, metformin, phenformin, etc. are known as biguanides, but there has been no reported use of them for culturing animal cells. Since biguanides are stable even at high temperature, they can be added to a synthetic basal medium and autoclaved together with the medium. The amount of buformin to be added is about 0.005–5 mg per liter of the medium in the form of a hydrochloride, preferably about 0.01–1 mg per liter. Like acetoacetic acid, buformin hydrochloride produces a cell growth promoting effect or antibody production enhancing effect when added in an extremely small amount, and an increase of the amount is likely to result in a decrease in such effect, though only a little.

Metformin can be used the same as buformin. The amount to be added is 0.1–100 mg per liter of the medium in form of a hydrochloride, preferably 1–30 mg per liter. Like acetoacetic acid, metformin produces a cell growth promoting effect or antibody production enhancing effect when added in an extremely small amount, and an increase of the amount is likely to result in a decrease in such effect, through only a little.

Vitamin $K_5$ to be used in the present invention is a substance obtained by reducing an oxime of vitamin $K_3$, and is usually sold in the form of a hydrochloride. Although vitamin $K_5$ and salts thereof are known as pharmaceutical materials and food preservatives, there has been no reported use of them for culturing animal cells. Since vitamin $K_5$ and salts thereof are also stable at high temperature, it is possible to autoclaved them together with a synthetic basal medium. The amount to be added is about 0.00005–0.1 mg per liter of the medium, preferably about 0.0001–0.01 mg per liter. Like acetoacetic acid, vitamin $K_5$ produces a cell growth promoting effect or antibody production enhancing effect when added in an extremely small amount, and an increase of the amount is likely to result in a decrease in such effect, though only a little.

N-acetyl-L-glutamic acid to be used in the present invention is sold in the form of a sodium salt or a potassium salt. There has been no reported use of N-acetyl-L-glutamic acid for culturing animal cells. Since N-acetyl-L-glutamic acid and salts thereof are also stable at high temperature, they can be autoclaved together with a synthetic basal medium. The amount to be added is about 1–200 mg per liter of the medium, preferably about 10–100 mg per liter. N-acetyl-L-glutamic acid tends to improve cell density and antibody production in proportion to the amount added, but at a concentration of 50 mg per liter or more, the effect produced does not vary significantly.

Each of the above-mentioned substances is added alone or in combination with other substances to a synthetic basal medium, and then used for culturing animal cells. With respect to the combined use, a combination of D-penicillamine with N-acetyl-L-glutamic acid produces an effect of expanding the range of cultured cell density. Furthermore, a combination of acetoacetic acid, biguanides, and vitamin $K_5$ makes it possible to reduce the amount of insulin added to a medium or even omit the addition of insulin thereto. The repression of the amount of insulin added thereto is an important term for the realization of a low protein medium or even a protein-free medium.

With respect to synthetic basal media, a number of media widely used for culturing animal cells can be cited. They include MEM and RPMI1640 medium already referred to, BME medium (basal medium of Eagle), and modified BME media such as DME medium (Dulbecco's modified Eagle's medium) and IMDM (Iscove's modified Dulbecco's medium).

These synthetic basal media contain inorganic salts, such as $CaCl_2$, $MgSO_4$, KCl, $KNO_3$, $NaHCO_3$, NaCl, $NaH_2PO_4$ and $Na_2O_3Se$; amino acids, such as L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine; vitamins, such as D-biotin, choline chloride, folic acid, myo-inositol, nicotinamide, calcium D-pantothenate, pyridoxal, riboflavin, thiamin and vitamin $B_{12}$; and carbohydrates, such as saccharides including D-glucose. They further contain, if necessary, buffer components such as HEPES, and other components such as phenol red, pyruvates and so forth.

In addition to the above-mentioned additives to a synthetic basal medium, known cell growth promoting, substances may be used in combination. They include nucleosides, 2-ketoglutaric acid (2-oxoglutaric acid), fructose, galactose, glycerophosphoric acid, citric acid, ethanolamine, para-aminobenzoic acid, iron-containing compounds, such as $FeSO_4$ and hemin, benzamidine, putrescine, and unsaturated fatty acids, such as oleic acid and linolic acid. Furthermore, in order to prevent the contamination of a medium with bacteria or mycoplasmas, antimicrobial agents, such as streptomycin, nystatin, gentamicins, ciprofloxacin, norfloxacin and levofloxacin, may be used in combination with the additives. The medium of the present invention for culturing animal cells can be made serum free by appropriately using some of the above-mentioned known cell growth promoting substances in combination. In a more preferred embodiment of the present invention, the cultivation of animal cells is possible without addition of any protein components to the medium. Examples of components which enable the protein-free cultivation of animal cells are given in the table below.

TABLE 1

| Important components in serum-free cultivation (mg/l) | |
|---|---|
| Ethanolamine.HCl | 1–10 |
| FeSO$_4$.7H$_2$O | 0.1–5 |
| EDTA.Fe.Na | 0.2–10 |
| Effective components in serum-free cultivation (mg/l) | |
| Fructose | 500–5000 |
| Galactose | 100–1000 |
| Sodium glycerophosphate.5.5H$_2$O | 50–1000 |
| D-penicillamine(*) | 5–500 |
| N-acetyl-L-glutamic acid(*) | 10–100 |
| Citric acid.H$_2$O | 10–100 |
| Metformin.HCl(*) | 0.1–100 |
| Buformin.HCl(*) | 0.01–1 |
| para-Aminobenzoic acid | 0.1–25 |
| Benzamidine.HCl | 0.1–2 |
| Putrescine.2HCl | 0.1–1 |
| Sodium oleate | 0.05–0.5 |
| Sodium linolate | 0.02–0.2 |
| Vitamin K$_3$(*) | 0.0001–0.01 |
| 2-Ketoglutaric acid | 10–100 |
| Succinic acid | 10–100 |
| Lithium acetoacetate(*) | 0.01–10 |
| Sodium thioglycolate | 5–100 |
| Zinc sulfate.7H$_2$O | 0.01–0.1 |
| L-thioproline | 1–5 |
| L-cysteine | 5–50 |
| Glutathione | 0.2–2 |
| Cocarboxylase | 0.02–0.2 |

Note: Those marked with (*) are components of the present invention.

In the cultivation of animal cells according to the present invention, when protein-free is not aimed at, hormons and growth factors, such as albumin, insulin, transferrin, epidermal cell growth factor and lipoproteins, may be added to a medium.

Among all, the addition of insulin has many advantages. The medium of the present invention for culturing animal cells is able to support the growth of a wide variety of cells, and yet, in some cases, the cultivation support ability of the medium may be dramatically improved by the addition of insulin. For example, as described later in a preferred embodiment of the present invention, excellent results have been obtained in the cultivation of unadapted HeLa cells. Those results of cultivation are by far superior to the results obtained with a serum-added medium. When insulin is added to a medium, the concentration should be in the range of 0.001–20 mg per liter of the medium, preferably 1–10 mg per liter. Since insulin is a hormone which exhibits physiological activities regardless of animal species, it is not necessarily required to select a suitable insulin according to the animal species of the cells to be cultured. Since swine insulin and bovine insulin are sold, such insulin may be added to the medium aseptically regardless of the origin of the cells to be cultured. In addition to those insulins which are extracted from animals, recombinant insulins may also be used.

With the use of the medium of the present invention, a wide variety of animal cells can be cultured. Examples of these cells include established cell lines of Namalwa, CHO-K$_1$ (SC), HeLa, COS7, BHK-21C13-2P, Vero, C127, human B lymphoblast and fibroblast which are frequently used as transformed host cells for the production of useful substances or in various biological experiments. In addition, it is also possible to culture myeloma cells, such as P3-X63-Ag8.653 and NS-1, which are frequently used as parent cells for cell fusion with the medium of the present invention. Needless to say, according to the present invention, it is also possible to culture those hybridomas which are obtained by the fusion of the above-mentioned cells with various lymphocytes, splenic cells or the like, as well as those cells which are transformed with a foreign gene.

According to the present invention, even if a protein-free medium is used in culturing animal cells, the adaptation operation generally required is not necessarily demanded. In other words, cells may be directly passaged from a conventional serum-added medium to the medium of the present invention. In cases where the cultivation of cells should be continued for a long period, it will often lead to better results to inoculate the cells without adaptation. On the other hand, if a sharp rise in cell density is expected at the initial stage of the culture, it is preferred that the cells be inoculated after adaptation.

In one aspect of the present invention, there is provided a method for enhancing antibody production of antibody-producing cells, comprising adding to a medium for the cells the aforementioned substances. The "antibody-producing cells" used in the present invention include hybridomas between antibody-producing cells and myeloma cells or the like, antibody-producing cells which have been transformed with EB virus (Epstein-Barr virus), and animal cells which have been transformed with an expression vector for the immunoglobulin gene. The above-mentioned substances not only promote the growth of these cells but also enhance the antibody production thereof.

Since the present invention supports the growth of a wide variety of cells, it is useful in the production of not only antibodies but also animal cells themselves and physiologically active substances other than antibodies. Examples of the production of animal cells themselves include the preparation of epitope-expression cells for detecting virus antibodies, the cultivation of pancreatic or hepatic cells for treating organs which have lost their functions, and the preparation of cells as a material for the study of ligand receptors such as hormones. On the other hand, the Cultivation of animal cells to obtain substances produced by the cells has an extremely wide range of application. In addition to antibodies, cytokines, hormones, growth factors, enzymes, virus antigens and the like are produced by culturing animal cells. Examples of these physiologically active substances are given below.

Examples of Cytokines
Interferon (IFN) α, β, γ
Tumor necrosis factor (TNF)
Lymphotoxin (LT)
Interleukin (IL) 1–13
Glanulocyte colony-stimulating factor (G-CSF)
Macrophage colony-stimulating factor (M-CSF)
Glanulocyte macrophage colony-stimulating factor (GM-CSF)
Stem cell factor (SCF)
Leukemia inhibitory factor (LIP).
Examples of Hormones
Erythropoietin (EPO)
Growth hormone (GH)
Insulin-like growth factor (IGF) 1, 2.
Examples of Growth Factors
Nerve growth factor (NGF)
Epidermal cell growth factor (EGF)
Fibroblast growth factor (FGF)
Hepatocyte growth factor (HGF)
Platelet-derived growth factor (PDGF)
Vascular endothelial cell growth factor (VEGF).
Examples of Virus Antigens
Human immunodeficiency virus (HIV) 1–2
Human hepatitis B virus (HBV)

Human hepatitis C virus (HCV)
Herpes simplex virus (HSV)
Cytomegalovirus (CMV)
Adult T cell leukemia virus (ATLV)
Varicella virus
Vaccinia virus
Coxsackievirus
Poliovirus
Coronavirus
Influenza virus
Rabies virus
Japanese encephalitis virus
Rubella virus
Measles virus
Parainfluenza virus
Sendai virus
Rota virus.

Each of the substances to be used in the present invention promotes the growth of animal cells according to the mechanism of action of its own. The following matters can be presumed for the mechanism of action of each component.

D-penicillamine exhibits an action of promoting the growth of animal cells through protecting the S—S bonds of proteins or adjusting oxidation-reduction potentials in the cells. Although the use of D-penicillamine as a mitogen on B cells has been reported, but its growth-promoting action on established cell lines has not been known. Furthermore, it has been confirmed that D-penicillamine has an action of preventing cell death when cell density is small. Generally, in the cultivation of animal cells, cell death tends to increase as cell density decreases. D-penicillamine has an action of inhibiting such a phenomenon. The action of D-penicillamine to prevent cell death at a low cell density is reinforced when citric acid, a known medium component, is used in combination. Concretely, when D-penicillamine has been added to a medium, the survival ratio does not decrease even at an extremely low cell density of $1 \times 10^3$ cells/ml or below. On the other hand, in a conventional serum-free medium, the survival ratio begins to decrease at a cell density of $1 \times 10^5$ cells/ml or below.

With respect to the enhancement of antibody production, D-penicillamine produces an action of stabilizing antibodies produced especially through the protection of S—S bonds.

Acetoacetic acid is a substance which will become a dose-limiting component for lipid synthesis in an environment where insulin is in short. The addition of this component to a medium makes it possible to reduce the amount of insulin added thereto, and thus contributes to the realization of a protein-free medium. Acetoacetic acid exhibits an action of cell growth promotion even in a medium to which no serum has been added, through facilitating lipid synthesis.

Biguanides, such as buformin hydrochloride, promote the sugar intake of cells in an environment where insulin is in short. Although there is something in common between this action and their action as a hypoglycemic agent, it is a completely novel finding that the sugar intake-promoting action of biguanides leads to promote the growth of animal cells.

Similar to biguanides, vitamin $K_5$ promotes the sugar intake of cells. Although the sugar intake-promoting action of vitamin $K_5$ has been confirmed in murine 3T3 cells, there has been no reported application of this action for promoting the growth of animal cells.

N-acetyl-L-glutamic acid has an action of increasing cell density in the cultivation of animal cells. N-acetyl-L-glutamic acid participates in the synthesis of carbamoyl phosphate in urea cycle (ornithine cycle), and is considered to increase cell density through the promotion of nitrogen metabolism to thereby promote cell growth.

With respect to the enhancement of antibody production, N-acetyl-L-glutamic acid produces an effect of increasing the production amount at least as a result of its actions of increasing the number of viable cells and prolonging the survival period of the cells in a similar manner seen in biguanides, vitamin $K_5$ and acetoacetic acid. However, in the data shown in Examples to be described later, there is observed an antibody production enhancing effect in N-acetyl-L-glutamic acid which cannot be explained only with the above-mentioned actions. In other words, a phenomenon has been observed that N-acetyl-L-glutamic acid clearly enhances antibody production in a situation where the number of cells has not necessarily been increased.

As described above, D-penicillamine or salts thereof, acetoacetic acid or salts thereof, biguanides, vitamine $K_5$ or salts thereof, and N-acetyl-L-glutamic acid or salts thereof exhibit a favorable cell growth promoting action when added to a medium alone, and this action is further enhanced when added to a medium together with at least one component selected from the group consisting of insulin, insulin-like growth factors, transferrin, iron compounds, ethanolamine, selenium compounds and citric acid.

According to the present invention, it is possible to obtain a medium for culturing animal cells to which no animal serum is added, i.e., a serum-free medium. Furthermore, since all of the growth promoting substances used in the present invention are chemically synthesized substances, it is possible to maintain the quality of the medium very easily. The easy maintenance of the quality of the medium is a great advantage from an economical viewpoint. In addition, since those substances are not derived from organisms, they are very unlikely to become a source of infection. Furthermore, since most of those substances are easy to sterilize, the medium of the present invention for culturing animal cells contributes to aseptic operation.

The present invention realizes not only a serum-free medium but also a low protein medium or even a protein-free medium which will make the purification of a useful substance extremely easy. In particular, when the medium of the present invention is used for culturing cells which produce immunoglobulin, the cost for immunoglobulin purification can be greatly reduced compared to the case of using a serum-added medium, because the former medium does not contain any other immunoglobulin.

The present invention provides not only cell growth promoting substances but also techniques to enhance the antibody-producing ability of antibody-producing cells. As confirmed in Examples, the composition of the present invention for enhancing the antibody production has an action of enhancing antibody production even on those cells which have not been adapted to a serum-free medium. Its effect of antibody production enhancement is more remarkable on those cells which have been adapted to a serum-free medium. Antibody production in a large quantity was confirmed, though the cell density was not significantly different from that on a serum-added medium.

Generally, an operation of adaptation is required in culturing animal cells. This operation is carried out when a cultural environment in which cells have been passaged is altered to a new one. Concretely, the cultural environment is gradually changed so that a target environment is finally obtained. For example, when those cells which have been passaged on a serum-added medium are to be inoculated into a serum-free medium, the cells are adapted by gradually decreasing the serum concentration in the medium. If this operation is omitted and the cultural environment is suddenly changed, a temporary decrease in the number of animal cells is often observed even if the new environment is a one which allows their culture. Also, depending on the medium, cases of cell destruction are not rare. In the cultivation of such delicate animal cells, the serum-free medium of the present invention sufficiently supports the growth of even those cells which have not been adapted, and furthermore a greater quantity of antibodies is produced with this medium compared to the case of using a serum-added medium. Therefore, the serum-free medium of the present invention can be said an excellent medium. From the viewpoint of adaptation operation for cells, the serum-free medium of the present invention can be said an easy to adapt medium which is less likely to cause a decrease in the number of cells or cell destruction.

In addition, the medium for culturing animal cells provided by the present invention has an effect of expanding the range of culturable cell density. In other words, the medium of the present invention widely supports the cultivation of cells of from low density to high density. Due to this effect, the medium makes it possible to continue the cultivation of cells without decreasing the survival ratio of the cells even at a low density where cell death is likely to increase on a conventional medium. On the other hand, the medium of the present invention also makes it possible to culture cells at a high density exceeding $1 \times 10^6$ cells/ml which is called saturation density for conventional media. Thus, the present invention provides a useful medium for culturing animal cells which expands the range of culturable cell density.

With the medium of the present invention for culturing animal cells, it is possible to culture not only antibody-producing cells but also a wide variety of animal cells. In particular, when insulin is added thereto, the medium provides a great advantage that the cultivation of cells can be started without adaptation operation in spite of serum-free cultivation. As so far described, the present invention provides an extremely useful medium which realizes a wide applicability under severe conditions of serum free.

DESCRIPTION OF THE PREFERRED EMBODIMENTS

Figure 1:
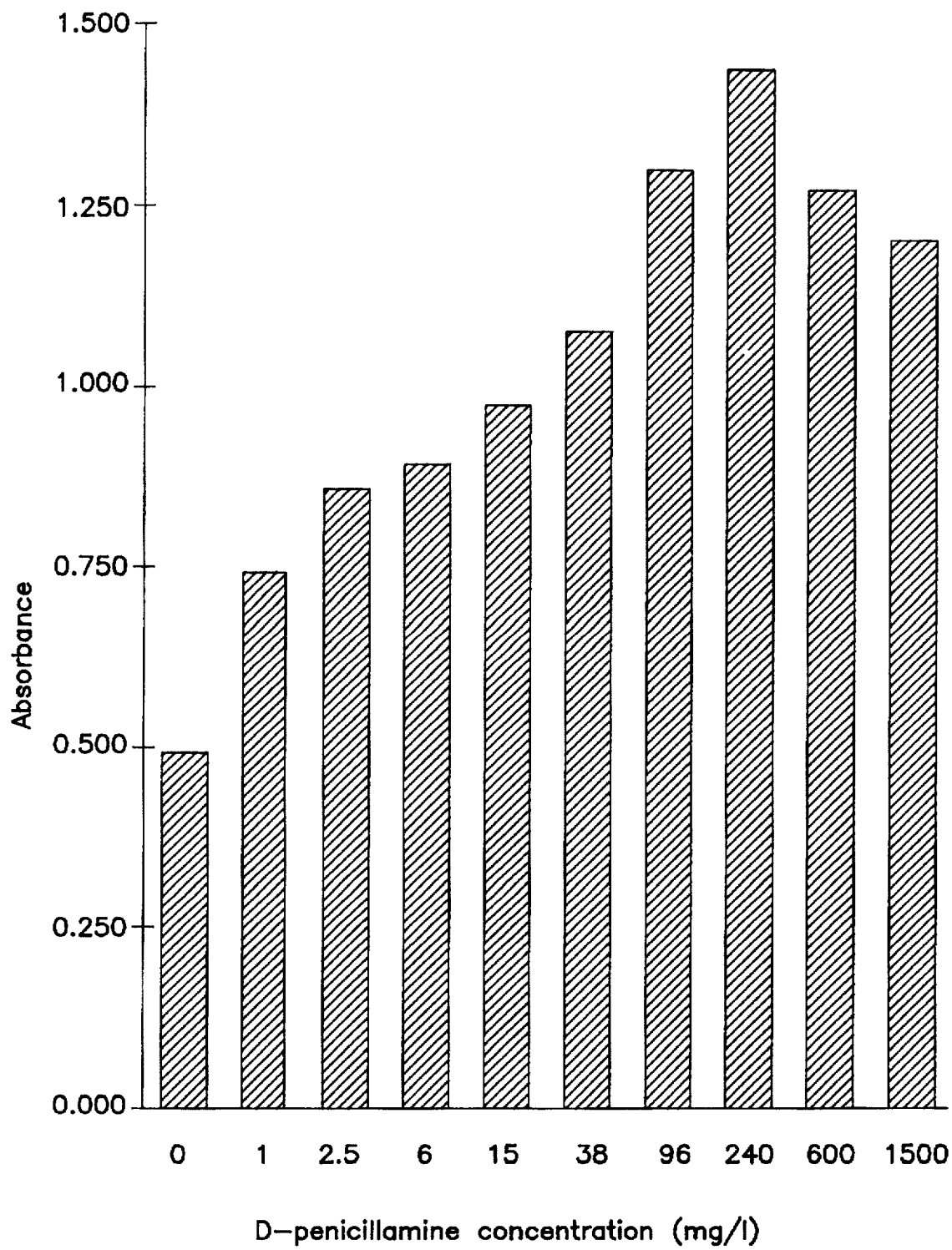
FIG. 1 is a graph showing the growth of cells on D-penicillamine-added IMDM. In this graph, the vertical axis represents absorbance, and the horizontal axis D-penicillamine concentration.

The present invention will now be described in more detail with reference to Examples.

EXAMPLE 1

Cell Growth Promoting Effect of the Medium of the Present Invention

Experiments were carried out to study the effect of the growth promoting substances of the present invention when each of them are added alone to a medium.

D-penicillamine, lithium acetoacetate, buformin hydrochloride, metformin hydrochloride, vitamin $K_5$ and N-acetyl-L-glutamic acid were added alone to a synthetic basal medium. As to each of the resultant media, the ability to culture cells was compared to that of the synthetic basal medium to which no growth promoting substance had been added. Furthermore, with respect to lithium acetoacetate, buformin hydrochloride, metformin hydrochloride and vitamin $K_5$ which are associated with the metabolism of sugars and lipids, their effects were also examined in a comparative manner in two cases of with and without the addition of insulin.

The synthetic basal medium was prepared by adding 1 mg/l. of $FeSO_4$ and 3 mg/l. of ethanolamine to IMDM (manufactured by Sigma Co.) having the composition shown in Table 2 below. As to the cells, a cell line P3-X63-Ag8.653 (ATCC-CRL1580) which had been adapted to protein free cultivation was used.

TABLE 2

Composition of IMDM

| Inorganic salts (mg/l.) | |
|---|---|
| $CaCl_2.2H_2O$ | 219.0 |
| $MgSO_4$ | 97.67 |
| KCl | 330.0 |
| $KNO_3$ | 0.076 |
| $NaHCO_3$ | 3024.0 |
| NaCl | 4505.0 |
| $NaH_2PO_4$ | 109.0 |
| $Na_2O_3Se$ | 0.017 |
| Amino acids (mg/l.) | |
| L-alanine | 25.0 |
| L-arginine.HCl | 84.0 |
| L-asparagine.HCl | 28.4 |
| L-aspartic acid | 30.0 |
| L-cystine.2HCl | 91.24 |
| L-glutamic acid | 75.0 |
| L-glutamine | 584.0 |
| Glycine | 30.0 |
| L-histidine.HCl.$H_2O$ | 42.0 |
| L-isoleucine | 105.0 |
| L-leucine | 105.0 |
| L-lysine.HCl | 146.0 |
| L-methionine | 30.0 |
| L-phenylalanine | 66.0 |
| L-proline | 40.0 |
| L-serine | 42.0 |
| L-threonine | 95.0 |
| L-tryptophan | 16.0 |
| L-tyrosine.2Na.$2H_2O$ | 103.79 |
| L-valine | 94.0 |
| Vitamins (mg/l.) | |
| D-biotin | 0.013 |
| Choline chloride | 4.0 |
| Folic acid | 4.0 |
| Myo-inositol | 7.2 |
| Nicotinamide | 4.0 |
| Calcium D-pantothenate | 4.0 |
| Pyridoxal.HCl | 4.0 |
| Riboflavin | 0.4 |
| Thiamin.HCl | 4.0 |
| Vitamin $B_{12}$ | 0.013 |
| Other components (mg/l.) | |
| D-glucose | 4500.0 |
| HEPES | 5958.0 |
| Sodium salt of phenol red | 16.0 |
| Sodium pyruvate | 110.0 |

As to N-acetyl-L-glutamic acid, the number of cells grown on the relevant medium was counted to investigate into the influence of this substance upon cell density (according to the cell counting method described below). As to the other cell growth promoting substances, their cell growth promoting effect was confirmed by measuring, as the indicator of viable cells, the production of formazane coupounds (with a dark blue color) resulted from the decomposition of MTT [3-(4,5-dimethylthiazol)-2,5-diphenyltetrazolium bromide)] (according to the MTT method described below).

(a) MTT Method

First, a cell suspension was seeded into each well of a 96-well microplate to give a concentration of $2.0 \times 10^4$ cells/50 µl/well, and then 50 µl of the medium was added to each well. The cells were incubated at 37° C. under an atmosphere of 5% $CO_2$ for 3 days. Then, 20 µl of 5 mg/ml MTT was added to each well and the cells were further incubated for 5 hours. Next, 100 µl of 10% sodium dodecyl sulfate (0.01N HCl solution) was added to each well and the cells were incubated at 37° C. overnight. After incubation, absorbance was measured at 540–680 nm. The cell growth promoting substances were used in the following amounts: 0–1,500 mg/l. for D-penicillamine, 0–10 mg/l for lithium acetoacetate, 0–10 mg/l. for buformin hydrochloride, 0–250 mg/l. for metformin hydrochloride, and 0–0.1 mg/l. for vitamin $K_5$.

Figure 2:
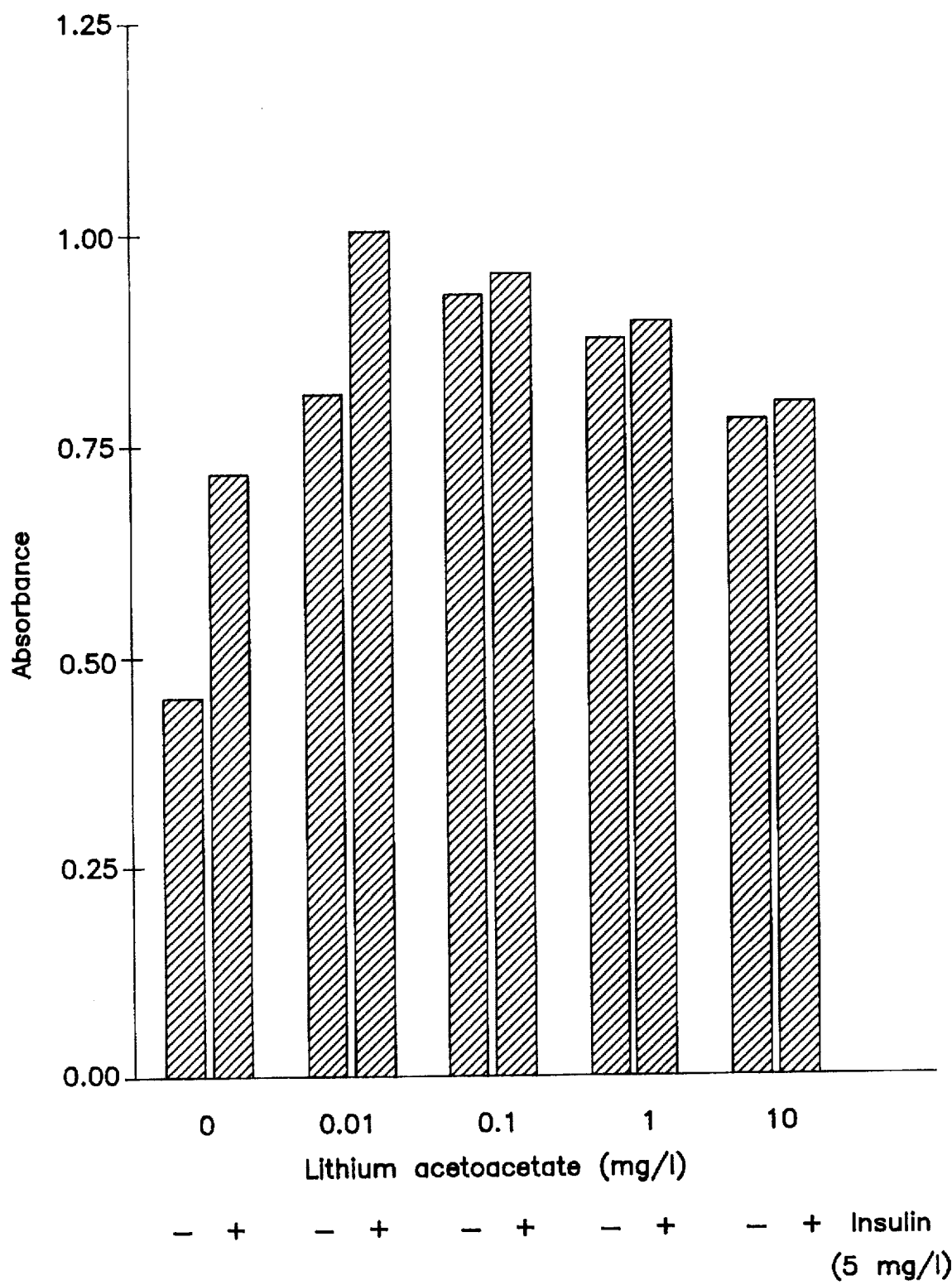
FIG. 2 is a graph showing the growth of cells on lithium acetoacetate-added IMDM. In this graph, the vertical axis represents absorbance, and the horizontal axis lithium acetoacetate concentration as well as the presence of insulin.
Figure 3:
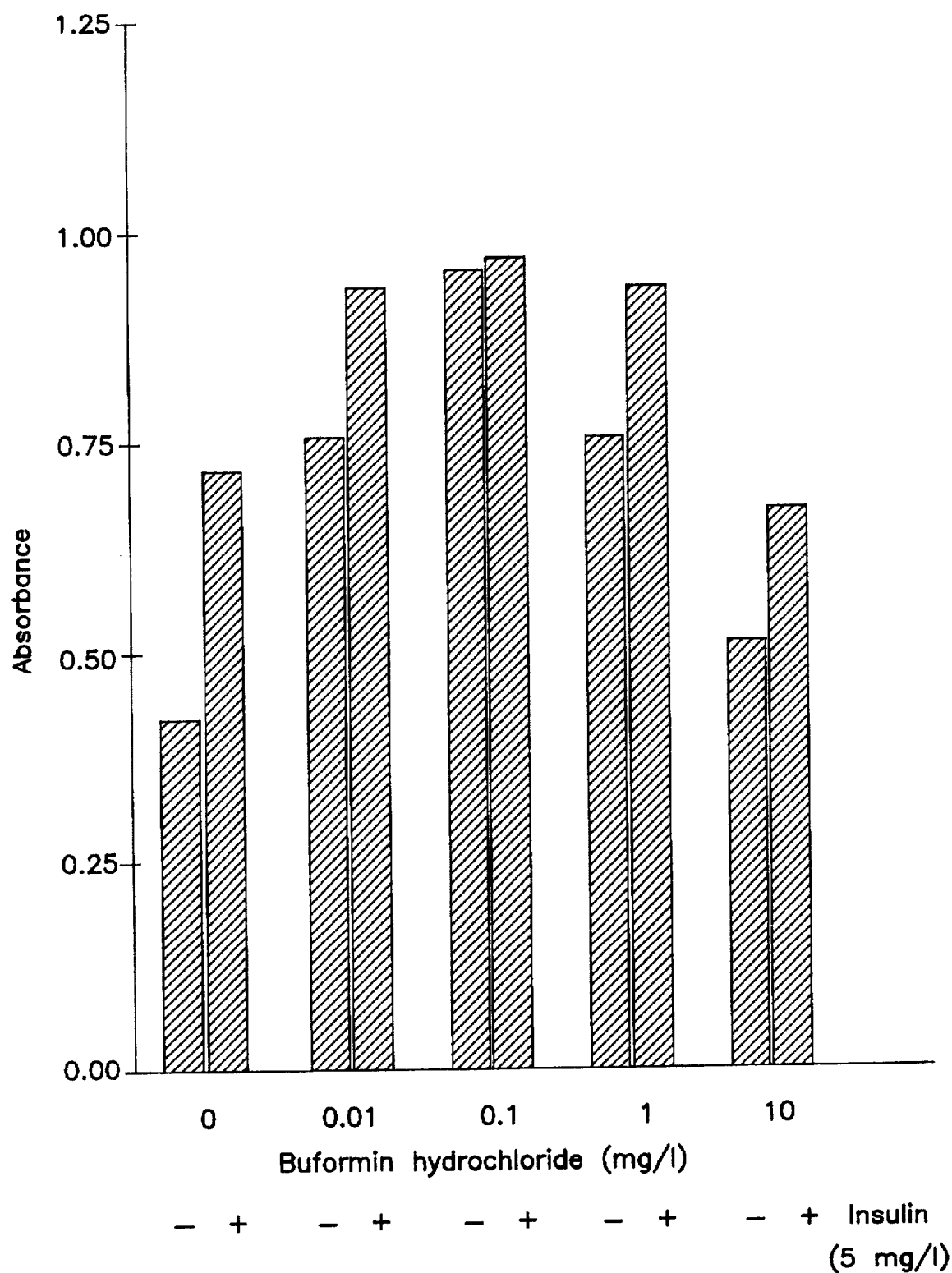
FIG. 3 is a graph showing the growth of cells on buformin hydrochloride-added IMDM. In this graph, the vertical axis represents absorbance, and the horizontal axis buformin hydrochloride concentration as well as the presence of insulin.
Figure 4:
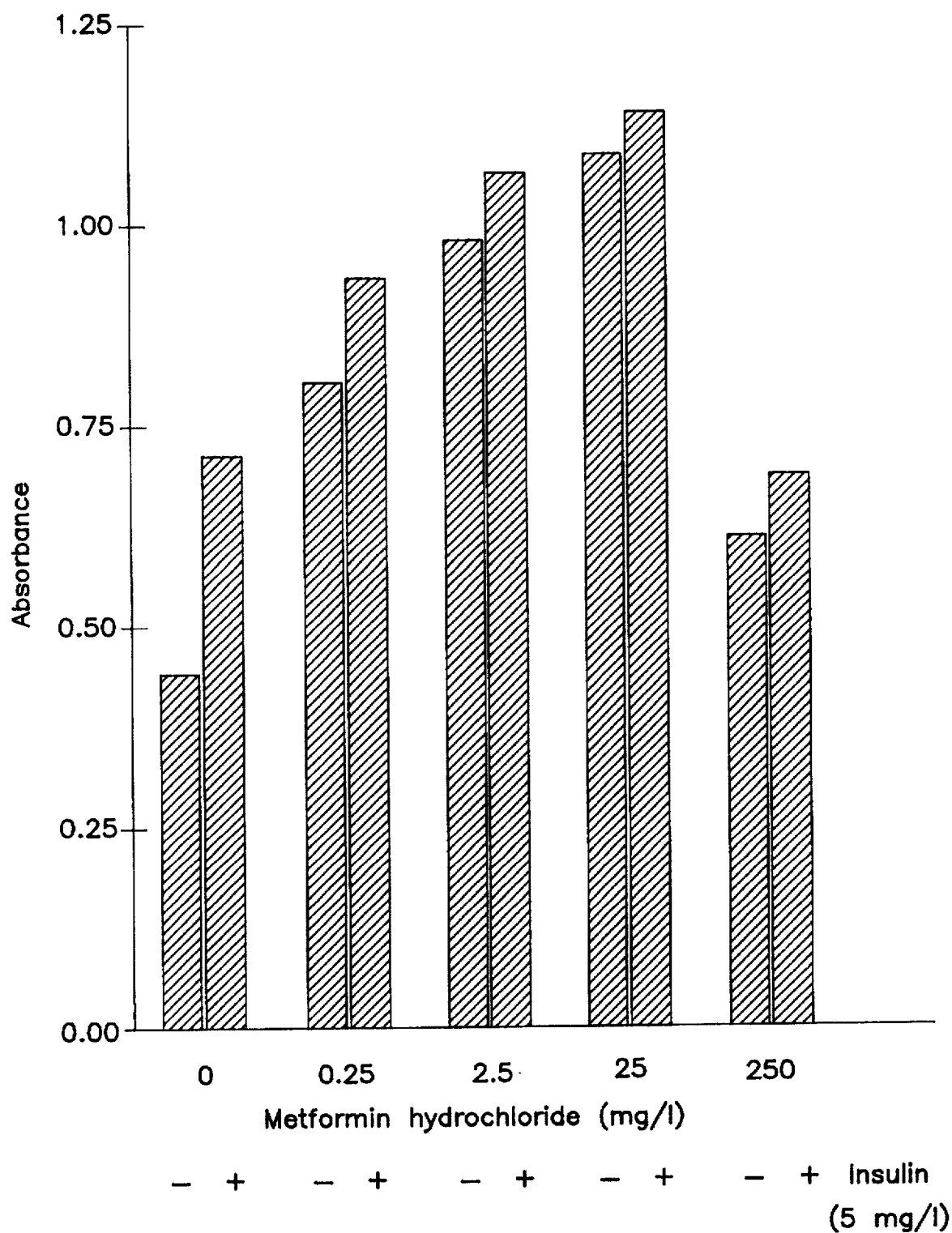
FIG. 4 is a graph showing the growth of cells on metformin hydrochloride-added IMDM. In this graph, the vertical axis represents absorbance, and the horizontal axis metformin hydrochloride concentration as well as the presence of insulin.
Figure 5:
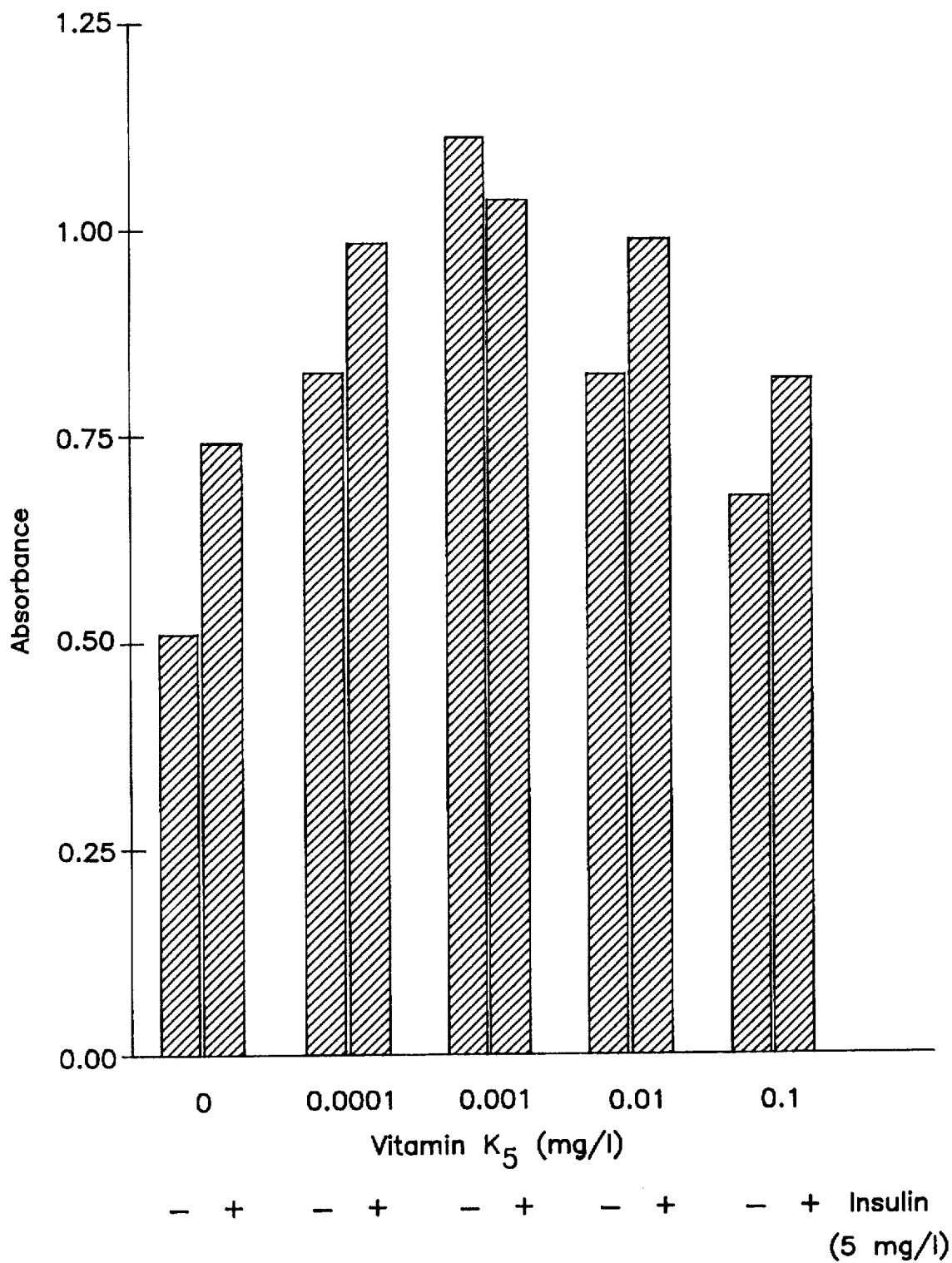
FIG. 5 is a graph showing the growth of cells on vitamin $K_5$-added IMDM. In this graph, the vertical axis represents absorbance, and the horizontal axis vitamin $K_5$ concentration as well as the presence of insulin.

The results are shown in FIG. 1 (D-penicillamine), FIG. 2 (lithium acetoacetate), FIG. 3 (buformin hydrochloride), FIG. 4 (metformin hydrochloride) and FIG. 5 (vitamin $K_5$). Lithium acetoacetate, buformin hydrochloride, metformin hydrochloride and vitamin $K_5$ respectively revealed a superior growth promoting effect to the effect of insulin when added alone. These results demonstrate that those growth promoting substances can be used as a substitute for insulin.

D-penicillamine exhibited a cell growth promoting effect proportional to the amount added up to a concentration of 240 mg/l (FIG. 1). Even at a higher concentration than this, it was confirmed that this substance clearly promotes cell growth compared to the case where this substance is not used. Metformin hydrochloride also exhibited a cell growth promoting effect proportional to the amount added up to a concentration of 25 mg/l, but an inhibitory action was observed at a concentration of 250 mg/l (FIG. 4).

(b) Cell Counting Method

In order to confirm the improvement of cell density by N-acetyl-L-glutamic acid, an experiment was carried out using cell counting techniques. The procedures were as follows.

P3-X63-Ag8.653 which had been grown on IMDM medium in advance was recovered by centrifugation and washed with the same medium 3 times. Then, the cell density was adjusted to become $1 \times 10^6$ cells/ml. This density is close to the saturation density on IMDM. A cell suspension was seeded into each well of a 96-well microplate in an amount of 50 µl in the same manner as in the MTT method. Then, 50 µl of IMDM containing N-acetyl-L-glutamic acid in varied concentrations of from 0 to 50 mg/l was added to each well. The cells were incubated at 37° C. under an atmosphere of 5% $CO_2$ for 1 to 6 days. Then, cells were stained with trypan blue and counted on a hemocytometer.

Figure 6:
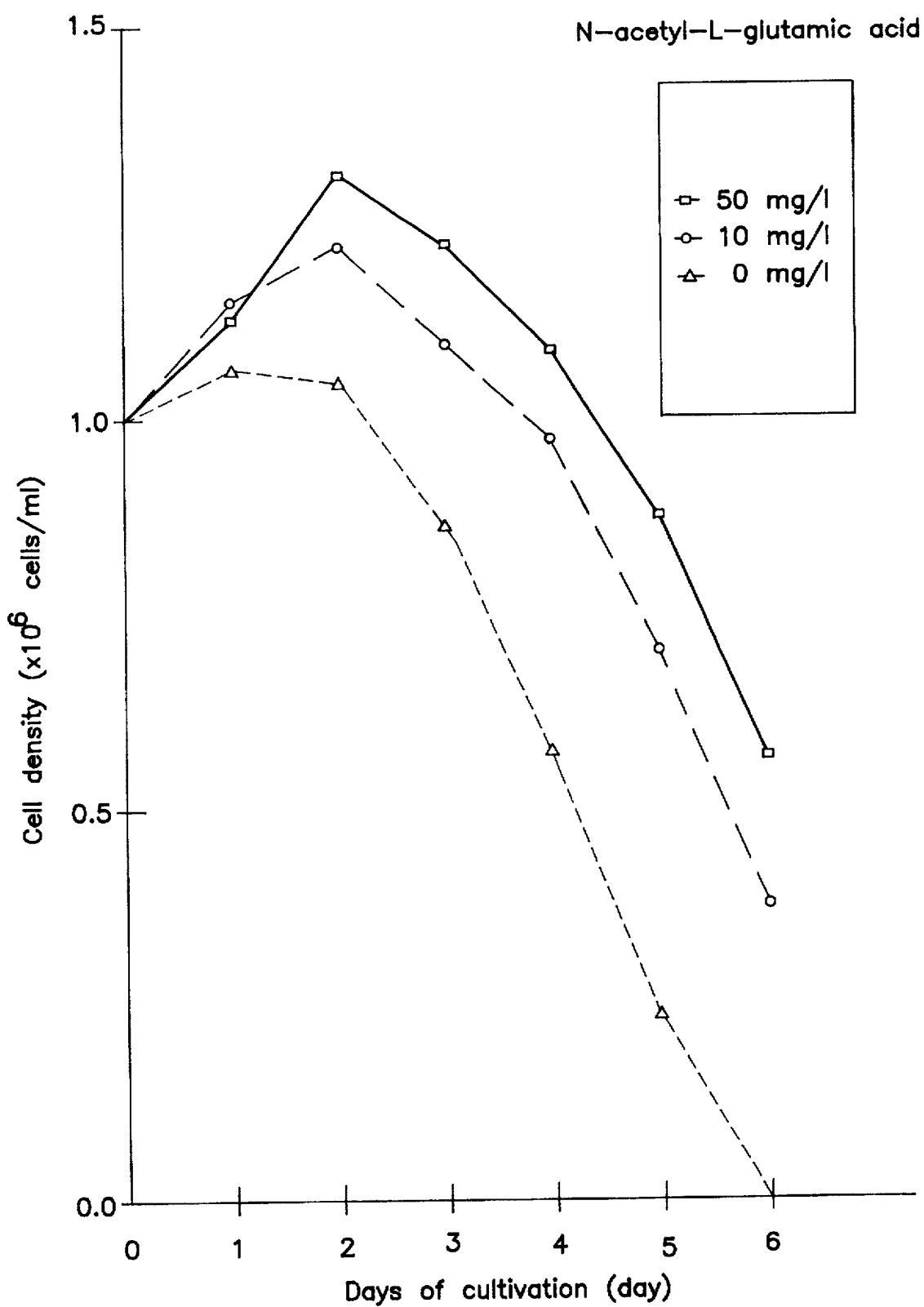
FIG. 6 is a graph showing the growth of cells on N-acetyl-L-glutamic acid-added IMDM. In this graph, the vertical axis represents cell density ($\times 10^5$ cells/ml), and the horizontal axis days of cultivation.

The results are shown in FIG. 6. On N-acetyl-L-glutamic acid-added media, cell density clearly increased. Since the cell density of $1 \times 10^6$ cells/ml is the saturation density on IMDM, a sudden drop of cell density is observed on day 2 of the cultivation and afterward on the medium to which no N-acetyl-L-glutamic acid has been added. On the other hand, on N-acetyl-L-glutamic acid-added media, cell growth continues up to day 2 of the cultivation exceeding the saturation density, and even on day 4, the cell density is maintained at around $1 \times 10^6$ cells/ml. Furthermore, the cell density on the not-added medium becomes almost zero at day 6 of the cultivation, while the N-acetyl-L-glutamic acid-added media maintain about one half of the cell density at the beginning of the cultivation. Thus, it has been confirmed that the addition of N-acetyl-L-glutamic acid is very effective in maintaining or improving cell density.

EXAMPLE 2

Antibody Production Enhancing Effect of the Medium of the Present Invention (1)

The antibody production enhancing effect of the medium according to the present invention was studied.

There was prepared a medium containing D-penicillamine, N-acetyl-L-glutamic acid, buformin hydrochloride and vitamin $K_5$ which are included in the antibody production enhancing agents of the present invention. The antibody production supporting ability of this medium was compared to that of a serum (FCS)-added medium. As to cells, there were used an anti-carcinoembryonic antigen (CEA) monoclonal antibody-producing hybridoma (F36-54) and a transformed murine myeloma cell line P3-X63-Ag8.653. The hybridoma F36-54 was obtained by cell-fusing murine splenic cells immunized with CEA and murine myeloma cell line P3-X63-Ag8.653 by using polyethylene glycol, establishing through cloning, and passaging on IMDM medium containing 10% FCS. This hybridoma was used in the experiment without adaptation to a serum-free medium. On the other hand, in the transformation of murine myeloma cell line P3-X63-Ag8.653, there was used the human/mouse type anti-CEA chimeric antibody expression vector (pMH-CEA-gpt) which is disclosed in Japanese Patent Laid-Open Publication No. 4-166089. The resultant transformed cells were used after adaptation to serum-free cultivation.

A cell suspension was seeded into each well of a 96-well microplate to give a concentration of $2\times10^4$ cells/50 µl/well. Then, 50 µl of a medium was added to each well. The cells were incubated at 37° C. under an atmosphere of 5% $CO_2$ for 10 days. Cell density and antibody concentration in the supernatant were measured everyday. The measurement of cell density was carried out in the same manner as in (b), Example 1. The antibody concentration was measured with the RIA sandwitching technique using solid phase anti-murine IgG antibody and $^{125}$I-labelled anti-murine IgG antibody.

The compositions of the media used in the experiment were as follows.

(a) Serum-Added Medium

A serum-added medium was prepared by adding to the IMDM used as the basal medium in Example 1 10% v/v FCS aseptically through filter sterilization. As to the FCS, 50 lots of FCS were screened and the one which had the highest ability in cell growth promotion and antibody production support was used in the experiment.

(b) Serum-Free Medium (The Medium of the Present Invention)

A serum-free medium was prepared by adding to the IMDM used as the basal medium in Example 1 the components shown in Table 3. Out of the components shown in Table 3, D-penicillamine, N-acetyl-L-glutamic acid, buformin hydrochloride and vitamin $K_5$ are included in the antibody production enhancing substances of the present invention (marked with "*" in the Table), and the other components are known additives for use in serum-free cultivation. Incidentally, though data are not incorporated herein, the inventors of the present invention have confirmed that the cells used in this experiment cannot grow and die out on a medium which is prepared by adding to IMDM medium only ethanolamine and selenium which are the non-protein components of ITES (insulin, transferrin, ethanolamine, selenium), which are generally considered the essential components for a serum-free medium. As seen from Table 3, the medium used in the experiment is not only serum-free but also protein-free.

TABLE 3

Medium Composition of the Present Invention for the Confirmation of Antibody Production Enhancing Effect

| IMDM | (mg/l.) |
| --- | --- |
| Fructose | 2000 |
| Galactose | 500 |
| Glycerophosphoric acid | 500 |
| D-penicillamine(*) | 250 |
| N-acetyl-L-glutamic acid(*) | 50 |
| Citric acid | 50 |
| Ethanolamine | 10 |
| para-Aminobenzoic acid | 10 |
| $FeSO_4$ | 1 |
| Buformin hydrochloride(*) | 0.5 |
| Vitamin $K_5$(*) | 0.002 |

Figure 7:
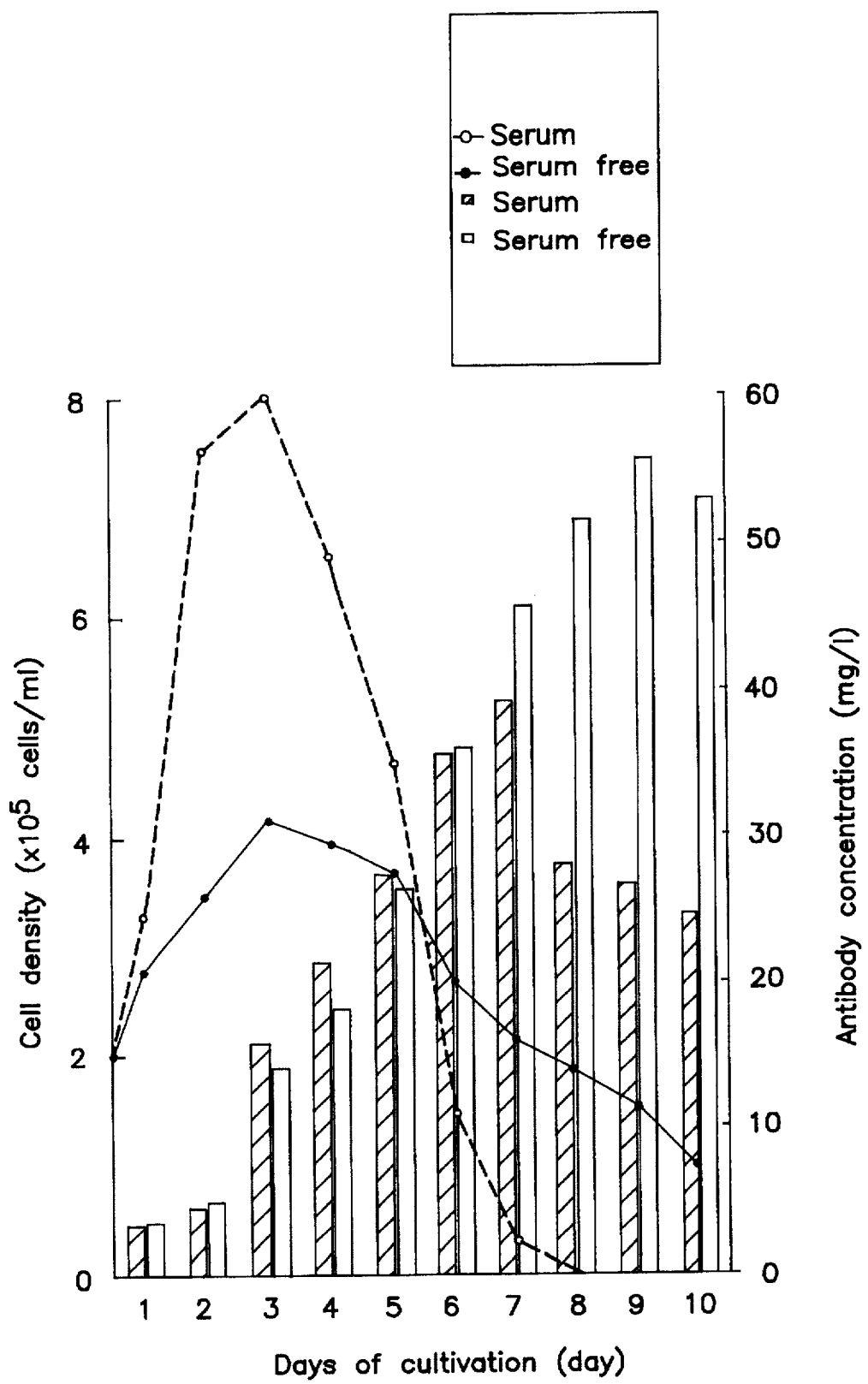
FIG. 7 is a graph showing the growth and antibody production of a hybridoma cell F36-54 on IMDM to which D-penicillamine, N-acetyl-L-glutamic acid, buformin hydrochloride and vitamin $K_5$ have been added. In this graph, the vertical axis at the left represents cell density ($\times 10^5$ cells/ml), the vertical axis at the right antibody concentration (mg/l), and the horizontal axis days of cultivation.
Figure 8:
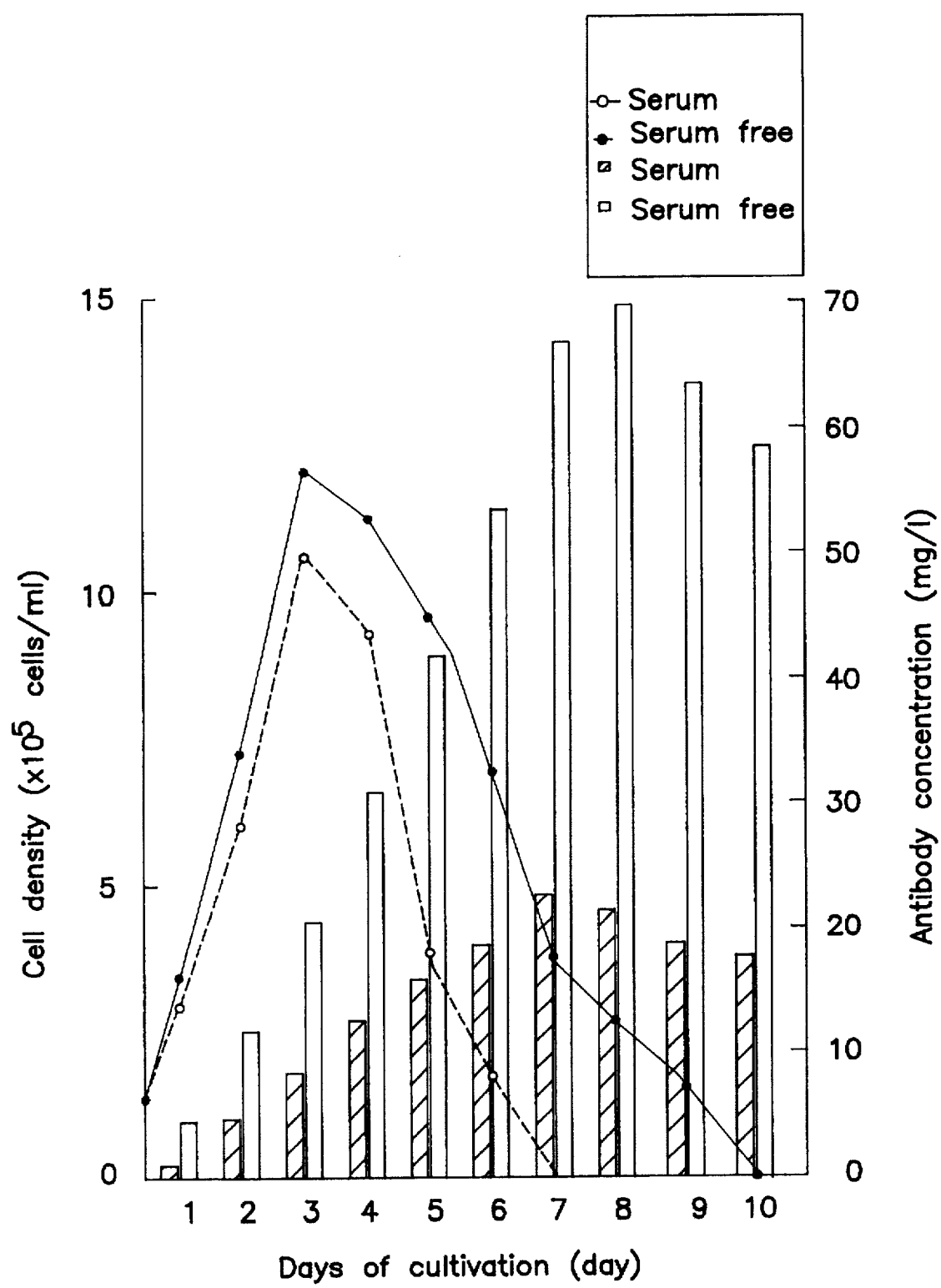
FIG. 8 is a graph showing the growth and antibody production of a transformed myeloma cell P3-X63-Ag8.653 on IMDM to which D-penicillamine, N-acetyl-L-glutamic acid, buformin hydrochloride and vitamin $K_5$ have been added. In this graph, the vertical axis at the left represents cell density ($\times 10^5$ cells/ml), the vertical axis at the right antibody concentration (mg/l), and the horizontal axis days of cultivation.

The results are shown in FIG. 7 (for hybridoma F36-54) and FIG. 8 (for transformed P3-X63-Ag8.653). In the cultivation of hybridoma F36-54, the amount of antibody production on the serum-free medium eventually excelled the amount on the serum-added medium during the course of cultivation in spite of the cleary lower cell density on the former medium. The cell density on the serum-free medium which was lower than that on the serum-added medium at the initial stage of the cultivation also excelled the cell density on the serum-added medium during the course of cultivation. These results are considered to be attributable to the fact that the cultivation of the hybridoma was started without adaptation of this cell line to the serum-free medium. It can be expected that, if the cultuvation is started after the adaptation of cells to a new medium to be used, as commonly practiced, the effect of the antibody production enhancing agents will be more remarkable.

In the cultivation of the transformed P3-X63-Ag8.653, a steady increase in cell density was observed from the beginning of the cultivation even on the serum-free medium, since the cell had been adapted thereto before use. Although big difference was not observed in the maximum cell density between the two media, there was extremely big difference in the amount of antibody production. According to the data on the days 7 and 8 of cultivation when difference in the amount of antibody production was greatest, the antibody concentration on the serum-free medium is even more than 3 times as much as that on the serum-added medium.

From these results, it has been confirmed that the antibody production enhancing effect on antibody producing cells according to the present invention is extremely great. While cycloheximide or the like referred to previously as a substance for inducing substance production has cytotoxicity also, the substance production enhancing components of the present invention are at the same time cell growth promoting components. Hence, it can be understood how useful the present invention is.

EXAMPLE 3

Antibody Production Enhancing Effect of the Medium of the Present Invention (2)

An experiment was carried out to study the antibody production enhancing effect of the medium of the present invention under the same conditions as in Example 2 except that the conditions of the hybridoma were changed.

An anti-CEA monoclonal antibody-producing hybridoma (F36-54) was used for the cultivation. In Example 2, this hybridoma was inoculated without adaptation. In this Example, comparison was attempted between the two cases of with adaptation and without adaptation.

A cell suspension was seeded into each well of a 96-well microplate to give a concentration of $2.0 \times 10^4$ cells/50 µl/well in the same manner as in Example 1. Then, 50 µl of a medium was added to each well. The cells were incubated at 37° C. under an atmosphere of 5% $CO_2$ for 10 days. Cell density and antibody concentration in the supernatant of a culture were measured everyday. The measurement of cell density was carried out in the same manner as in (b), Example 1. The antibody concentration was measured with the RIA sandwitching technique using solid phase anti-murine IgG antibody and $^{125}$I-labelled anti-murine IgG antibody.

The compositions of the media used in the experiment were the same as those used in Example 2.

Figure 9:
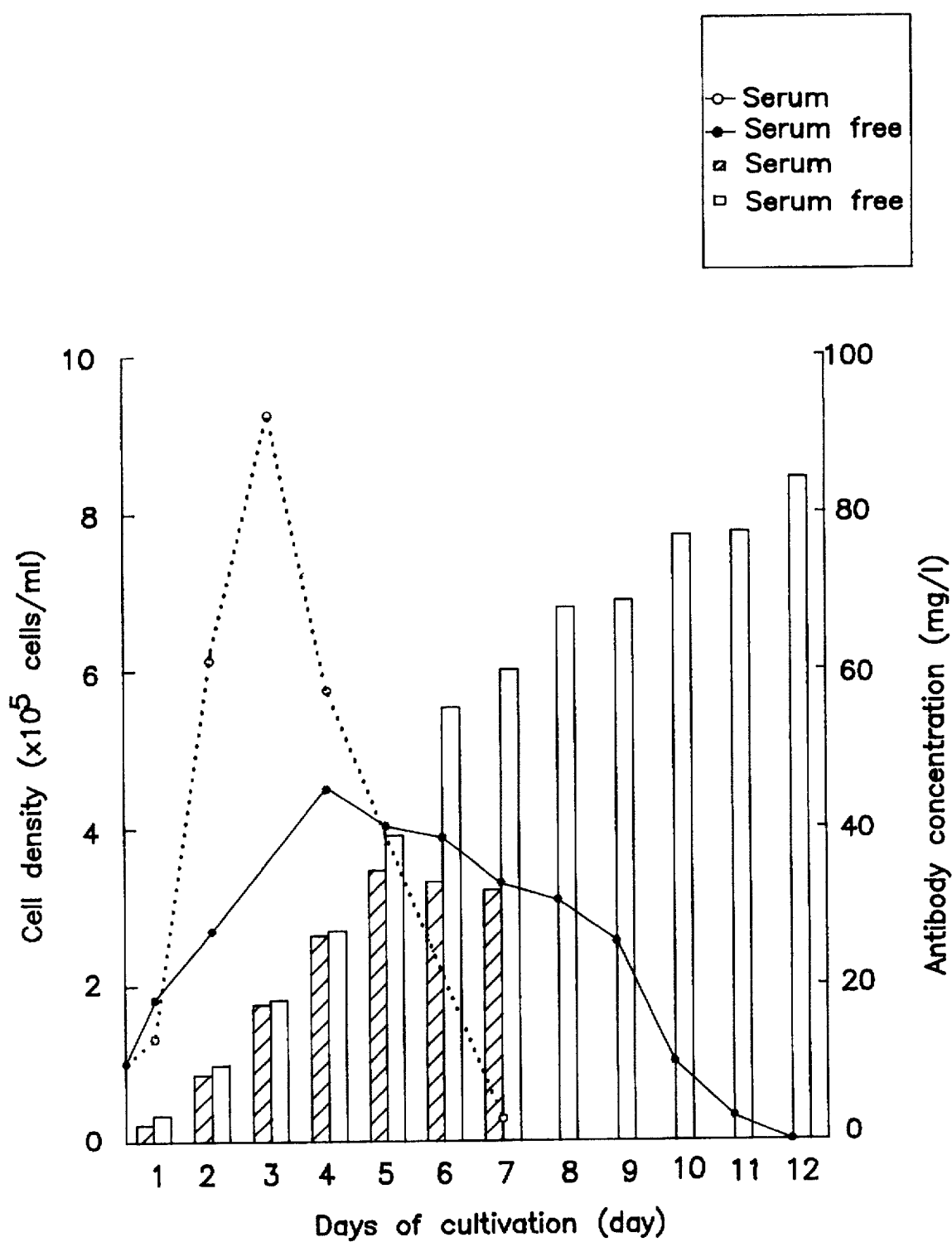
FIG. 9 is a graph showing the growth and antibody production of a hybridoma cell F36-54 (adapted) on IMDM to which D-penicillamine, N-acetyl-L-glutamic acid, buformin hydrochloride and vitamin $K_5$ have been added. In this graph, the vertical axis at the left represents cell density ($\times 10^5$ cells/ml), the vertical axis at the right antibody concentration (mg/l), and the horizontal axis days of cultivation.

The results with adapted cells are shown in FIG. 9. (Since the results with unadapted cells are identical with those obtained in Example 2, data is not shown.) Even after adaptaion, the cell density of hybridoma F36-54 progressed rather low at the beginning of the cultivation on the medium of the present invention, compared to the cell density on the serum-added medium. However, the amount of antibody production on the medium of the present invention increased during the course of cultivation, and eventually by far excelled the amount on the serum-added medium. The cell density on the medium of the present invention, which was lower than that on the serum-added medium at the initial stage of the cultivation, finally excelled the cell density on the serum-added medium. From the comparison of the results of with and without adaptation, it is clear that F36-54 can achieve still higher antibody production with adaptation. From these results, it has been confirmed that the antibody prodution enhancing effect on antibody-producing cells according to the present invention can be further increased by, in particular, adaptation operation.

EXAMPLE 4

Experiment of Culturing Various Animal Cells Using the Medium of the Present Invention This experiment was carried out to study the kinds of cells which can be cultured on the medium of the present invention.

The media used in the experiment were as follows: a medium whose composition (IMDM+D-penicillamine+N-acetyl-L-glutamic acid+buformin hydrochloride+vitamin $K_5$) is shown in Table 3 as a medium of the present invention, a medium obtained by adding 5 mg/l. of insulin to this medium, and 10% v/v FCS-added RPMI 1640 medium as a control. On these three medium, the 12 established cell lines listed below were cultured, and cultivation results of each cell line were compared. Difference in cultivation results due to the carrying out of adaptation was also observed.
Namalwa (ATCC-CRL1432)
Human B lymphoblast (peripheral blood lymphocytes infected with EB virus; EBV transformant)
ARH77 (ATCC-CRL1621)
NS-1 (ATCC-TIB18)
P3U1 (ATCC-CRL1597)
SP2/O (ATCC-CRL1581)
CHO-K1 (SC) (deposited at The Institute of Physical and Chemical Research, Japan, under Accession No. RCB-0403)
C127 (ATCC-CRL1616)
BHK-21C13-2P (RCB-0420)
COS7 (ATCC-CRL1651)
Vero (ATCC-CCL81)
HeLa (ATCC-CCL2)

A cell suspension was seeded into each well of a 96-well microplate to give a concentration of $2.0 \times 10^4$ cells/50 µl/well. Then, 50 µl of each medium was added thereto. The cells were incubated at 37° C. under an atmosphere of 5% $CO_2$ for 10 days, and cell density was measured everyday. The measurement was carried out in the same manner as in (b), Example 1.

Figure 10:
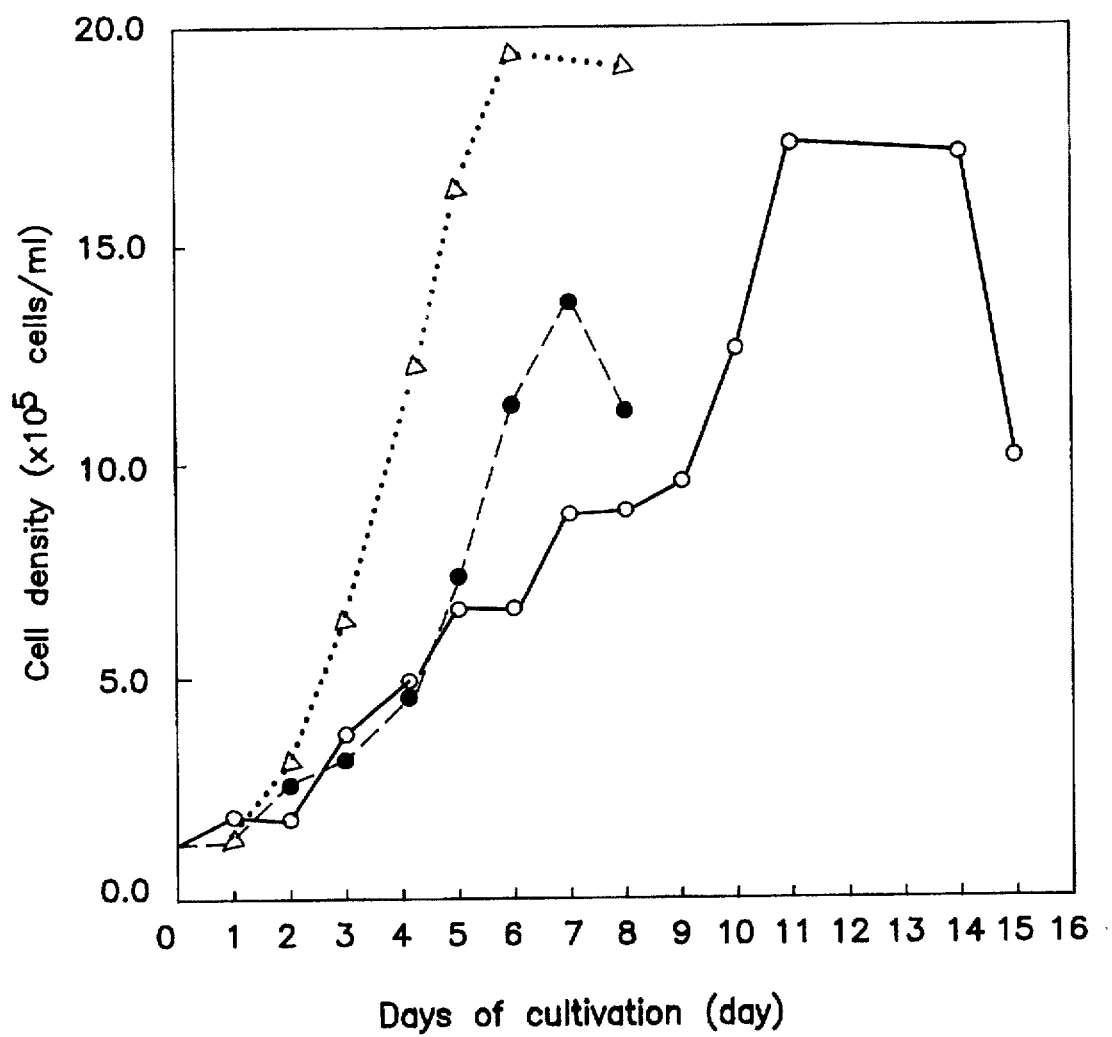
FIG. 10 is a graph showing the growth of Namalwa (unadapted) on the three media: IMDM to which D-penicillamine, N-acetyl-L-glutamic acid, buformin hydrochloride and vitamin $K_5$ have been added (—o—), a medium obtained by adding 5 mg/l of insulin to this IMDM (—●—), and RPMI 1640 medium to which 10% v/v fetal calf serum (FCS) has been added (—△—). In this graph, the vertical axis represents cell density ($\times 10^5$ cells/ml), and the horizontal axis days of cultivation.
Figure 11:
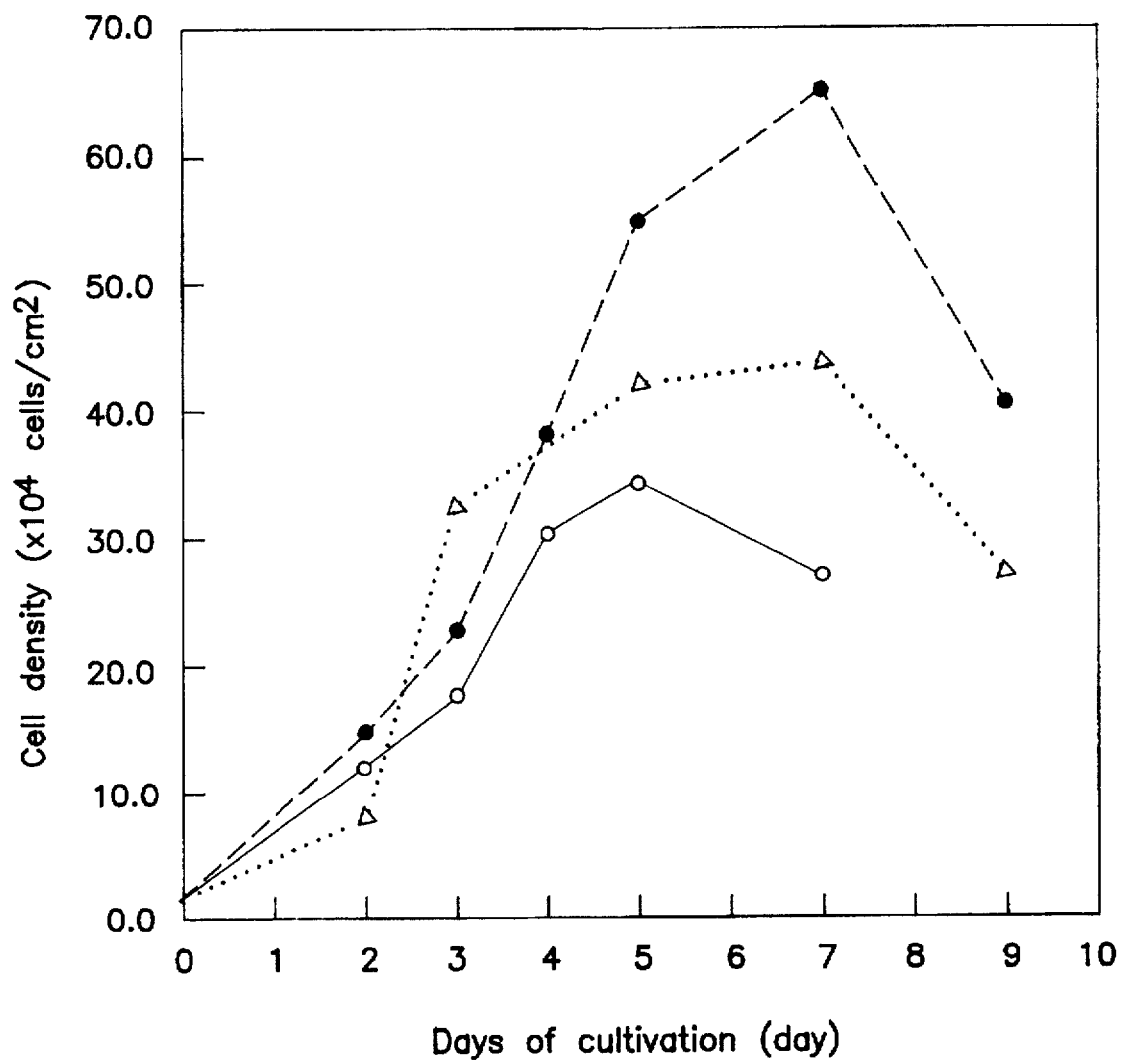
FIG. 11 is a graph showing the growth of HeLa (unadapted) on the three media: IMDM to which D-penicillamine, N-acetyl-L-glutamic acid, buformin hydrochloride and vitamin $K_5$ have been added (—o—), a medium obtained by adding 5 mg/l of insulin to this IMDM (—●—), and RPMI 1640 medium to which 10% v/v fetal calf serum (FCS) has been added (—△—). In this graph, the vertical axis represents cell density ($\times 10^4$ cells/cm$^2$), and the horizontal axis days of cultivation.
Figure 12:
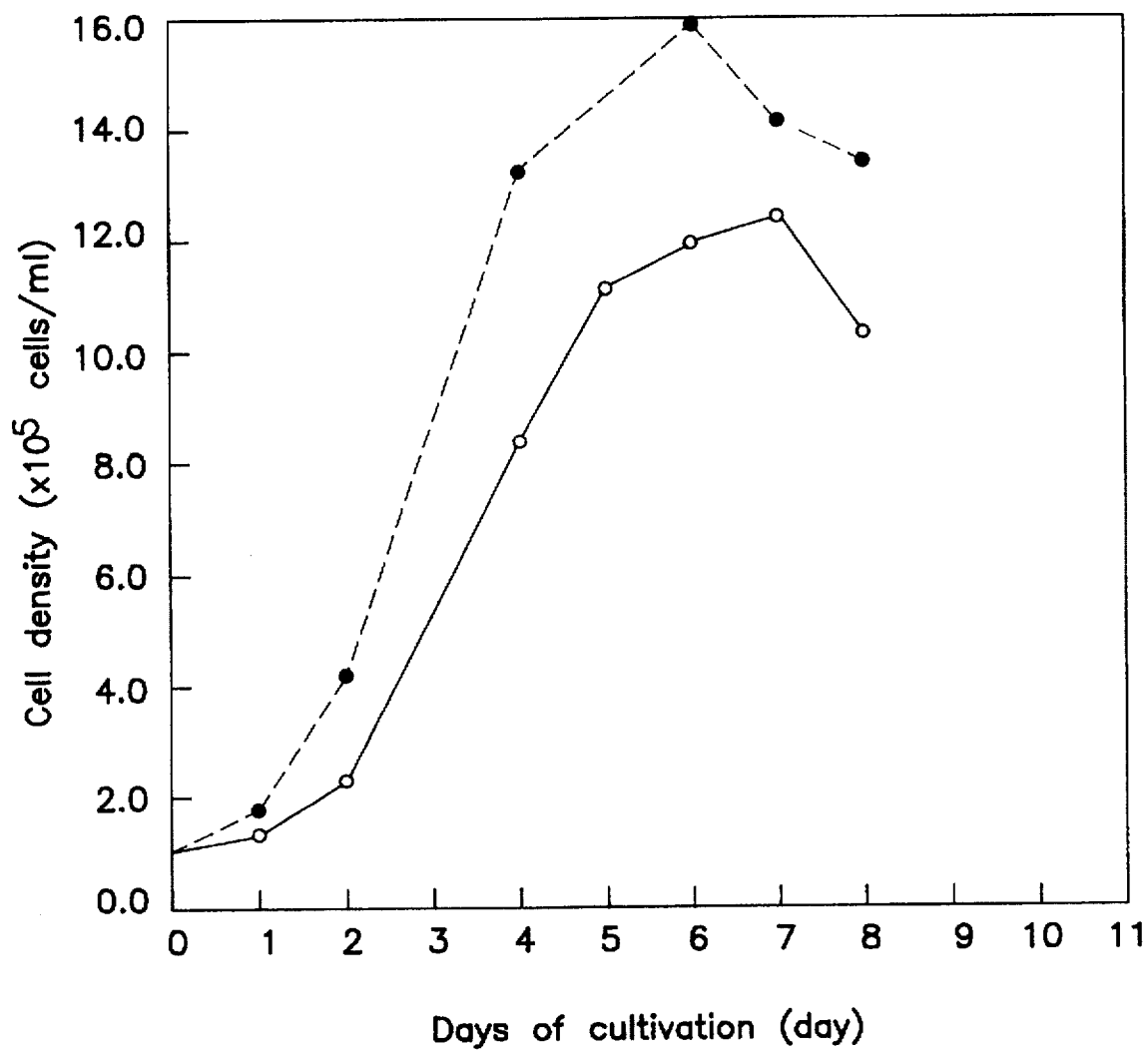
FIG. 12 is a graph showing the growth of BHK-21C13-2P (adapted) on two media: IMDM to which D-penicillamine, N-acetyl-L-glutamic acid, buformin hydrochloride and vitamin $K_5$ have been added (—o—) and a medium obtained by adding 5 mg/l of insulin to this IMDM (—●—). In this graph, the vertical axis represents cell density ($\times 10^5$ cells/ml), and the horizontal axis days of cultivation.

The results are shown in Table 4. It should be noted that in Table 4, the medium having the composition shown in Table 3 is expressed as "Protein free", and that the medium to which insulin has been added is expressed as "Insulin added". Many of the established cell lines used in this experiment have been proved to grow in a serum-added medium. On the medium of the present invention, a considerably large number of these cell lines can grow even without adaptation. With respect to those cell lines which exhibited particulary good cultivation results, growth curves thereof are shown in FIG. 10 (for Namalwa, unadapted), FIG. 11 (for HeLa, unadapted) and FIG. 12 (for BHK-21C13-2P, adapted). Since HeLa is an adhesive cell, the results were calculated as the number of cells per $cm^2$. Since the cultivation of a cell line was discontinued when the cell density was confirmed to have reached the saturation density, there are some growth curves in FIGS. 10–12 which are not drawn up to day 10 of cultivation.

From the results Namalwa is capable of completely protein-free cultivation even without adaptation. In the cultivation of HeLa, when insulin was added, the medium of the present invention achieved excellent cultivation results which were above the growth ability on the serum-added medium. It has been also confirmed that, with adaptation operation, BHK-21C13-2P reveals a growth ability on the medium of the invention which is very close to the growth ability on the serum-added medium.

These results demonstrate that the medium of the present invention sufficiently supports the cultivation of various animal cells in spite of being serum free. In addition, it has been confirmed that still favorable cultivation results can be obtained by adding insulin to the medium.

TABLE 4

Adaptability of Cells to Media

| | Before adaptation | | After adaptation | |
|---|---|---|---|---|
| | Protein free | Insulin added | Protein free | Insulin added |
| Namalwa | ◉ | ◉ | ◉ | ◉ |
| EBV transformant | ◉ | ◉ | ◉ | ◉ |
| ARH77 | ○ | ○ | ○ | ○ |
| NS-1 | Δ | Δ | ○ | ◉ |
| P3U1 | Δ | Δ | ○ | ◉ |
| SP2/0 | ○ | ◉ | ○ | ◉ |
| CHO-K1(SC) | ○ | ◉ | ○ | ◉ |
| C127 | Δ | ○ | ○ | ◉ |
| BHK-21C13-2P | ○ | ○ | ◉ | ◉ |
| COS7 | ○ | ○ | ○ | ◉ |
| Vero | Δ | ○ | ○ | ◉ |
| Hela | ○ | ◉ | ◉ | ◉ |

◉ Well grown
○ Growable
Δ Maintainable
X Dead

What is claimed is:

1. A medium composition comprising N-acetyl-L-glutamic acid or a salt thereof in combination with an animal cell culture medium which comprises, inorganic salts, saccharides, vitamins and amino acids.

2. The medium composition according to claim 1, which further comprises at least one of the group consisting of D-penicillamine or salts thereof, acetoacetic acid or salts thereof, biguanides and vitamin $K_5$ or salts thereof.

3. The medium composition according to claim 2, which is aqueous.

4. The medium composition according to claim 3, wherein the N-acetyl-L-glutamic acid is in an amount of from 1 to 200 mg per liter.

5. The medium composition according to claim 4, which further comprises acetoacetic acid or a salt thereof.

6. The medium composition for culturing animal cells according to claim 5, wherein the acetoacetic acid is in the form of a lithium salt in an amount of from 0.005 to 50 mg. per liter.

7. The medium composition according to claim 4, which further comprises vitamin $K_5$ or a salt thereof.

8. The medium composition according to claim 7, wherein the vitamin $K_5$ is in an amount of from 0.00005 to 0.1 mg per liter.

9. The medium composition according to claim 4, which does not contain serum.

10. The medium composition according to claim 9, which does not contain protein.

11. The medium composition according to claim 4, which further comprises at least one biguanide.

12. The medium composition according to claim 11, wherein said biguanide is selected from the group consisting of buformin, metformin, phenformin, and salts thereof.

13. The medium composition according to claim 12, wherein the buformin salt is buformin hydrochloride in an amount of from 0.005 to 5 mg per liter.

14. The medium composition according to claim 12, wherein the metformin salt is metformin hydrochloride in an amount of from 0.1 to 100 mg per liter.

15. The medium composition according to claim 4, further comprising D-penicillamine or a salt thereof.

16. The medium composition according to claim 15, wherein D-penicillamine or salt thereof is in an amount of from 0.5 to 5.000 mg per liter of medium composition.

17. A method for culturing animal cells comprising the steps of:

selecting animal cells, and culturing said cells in an aqueous culture medium comprising N-acetyl-L-glutamic acid or a salt thereof.

18. The method according to claim 17, wherein said cells are physiologically active.

19. The method according to claim 17, further comprising adding to said medium at least one of the group consisting of D-penicillamine or salts thereof, acetoacetic acid or salts thereof, biguanides and vitamin $K_5$ or salts thereof.

20. The method according to claim 17, wherein said animal cells are antibody-producing cells.

21. The method according to claim 20, wherein said antibody-producing cells are selected from the group consisting of hybridomas of antibody-producing cells and myeloma cells, cells transformed with a vector for expressing immunoglobulin gene, and antibody-producing cells transformed with EB virus.

22. A method for producing a physiologically active substance, which comprises the steps of:

selecting animal cells which produce said physiologically active substance;

culturing said animal cells in a medium comprising N-acetyl-L-glutamic acid or a salt thereof; and harvesting the cells grown or the physiologically active substance produced by the cells.

23. The method according to claim 22, wherein said physiologically active substance is selected from the group consisting of antibodies, cytokines, hormones, growth factors, enzymes and virus antigens.

24. The method according to claim 22, wherein said medium further contains at least one of the group consisting of D-penicillamine or salts thereof, acetoacetic acid or a salt thereof, biguanide and vitamin $K_5$ or a salt thereof.

* * * * *

UNITED STATES PATENT AND TRADEMARK OFFICE
CERTIFICATE OF CORRECTION

PATENT NO. : 5,719,050

DATED : February 17, 1998

INVENTOR(S): MAKOTO HASHIMOTO ET AL.

It is certified that error appears in the above-identified patent and that said Letters Patent is hereby corrected as shown below:

COLUMN 7
Line 31, "hormons" should read --hormones--.

COLUMN 9
Line 46, "short." should read --short supply.--;
Line 54, "short." should read --short supply.--;
Line 57, "leads to promote" should read --promotes--.

COLUMN 17
Line 14, "sandwitching" should read --sandwiching--.

COLUMN 19
Line 4, "comprises," should read --comprises--;
Line 17, "for culturing animal cells" should be deleted.

Signed and Sealed this

Fifteenth Day of February, 2000

Attest:

Q. TODD DICKINSON

Attesting Officer    Commissioner of Patents and Trademarks